(12) United States Patent
Leigh et al.

(10) Patent No.: US 8,889,189 B2
(45) Date of Patent: *Nov. 18, 2014

(54) DISSOLUTION COMPOSITION FOR EXAMINING DRUG SOLUBILITY

(71) Applicant: Phares Pharmaceutical Research N.V., Curaçao (AN)

(72) Inventors: Steve Leigh, Muttenz (CH); Mathew Louis Steven Leigh, Muttenz (CH); Peter Van Hoogevest, Bubendorf (CH); Daniel Streich, Münchenstein (CH); Jacques Quinton, Waldighoffen (FR)

(73) Assignee: Phares Pharmaceutical Research, N.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/652,837

(22) Filed: Oct. 16, 2012

(65) Prior Publication Data

US 2013/0055831 A1 Mar. 7, 2013

Related U.S. Application Data

(63) Continuation of application No. 12/084,806, filed as application No. PCT/EP2006/010809 on Nov. 10, 2006, now Pat. No. 8,287,907.

(30) Foreign Application Priority Data

Nov. 10, 2005 (GB) .................................. 0522942.2

(51) Int. Cl.
| | | |
|---|---|---|
| A61K 9/14 | (2006.01) | |
| A61K 9/08 | (2006.01) | |
| A61K 9/10 | (2006.01) | |
| A61K 47/12 | (2006.01) | |
| A61K 47/44 | (2006.01) | |
| G01N 33/15 | (2006.01) | |

(52) U.S. Cl.
CPC ............. *G01N 33/15* (2013.01); *Y10S 514/937* (2013.01); *Y10S 514/943* (2013.01)
USPC ........... 424/489; 424/499; 424/493; 424/502; 514/937; 514/943; 514/784; 514/785; 514/777; 514/773

(58) Field of Classification Search
CPC ........... G01N 33/15; A61K 9/10; A61K 9/14; A61K 9/1652; A61K 9/1658; A61K 47/36; A61K 47/42; A61K 47/44
USPC .......... 424/499, 502, 493; 514/937, 943, 784; 514/785, 777, 773
See application file for complete search history.

(56) References Cited

U.S. PATENT DOCUMENTS

| | | | |
|---|---|---|---|
| 4,156,719 | A | 5/1979 | Sezaki et al. |
| 5,747,066 | A | 5/1998 | Pittrof et al. |
| 5,759,445 | A | 6/1998 | Yamamoto et al. |
| 6,537,561 | B1 | 3/2003 | Fukui et al. |
| 6,846,801 | B1 | 1/2005 | Baeckstroem et al. |
| 2005/0152965 | A1 | 7/2005 | Betageri |

FOREIGN PATENT DOCUMENTS

| | | |
|---|---|---|
| CN | 1298702 | 6/2001 |
| WO | 9604916 A1 | 2/1996 |
| WO | 179773 | 10/2001 |

OTHER PUBLICATIONS

Dressman, Jennifer B. et al. "In vitro-in vivo correlations for lipophilic, poorly water-soluble drugs," Oct. 2000, European Journal of Pharmaceutical Sciences, vol. 11, Nr. Suppl. 2, pp. S73-S80 ISSN: 0928-0987.
Boni, Julia Elisabeth. "Improvements to biorelevant dissolution testing: lyophilized media, buffer alternatives and miniaturized apparatus," Aug. 13, 2009, Cuvillier, E. ISBN: 978-3-86955-079-4, p. 51.
Kloefer, Bastian et al. "Study of a Standardized Taurocholeate-Lecithin Powder for Preparing the Biorelevant Media FeSSIF and FaSSIF," Dissolution Technologies, Aug. 2010.
USPC Official Oct. 1, 2010-Jan. 31, 2011 General Chapters "Powder Flow: Angle of Repose." pp. 1-8.
Porter, Christopher J.H. and Charman, William N. "In Vitro Assessment of Oral Lipid Based Formulations." Advanced Drug Delivery Reviews 50 (2001): pp. S127-S147.
Leuenberger, H. "Spray freeze-drying—the process of choice for low water soluble drugs?" Journal of Nanoparticle Research 4 (2002); pp. 111-119.
Griseofulvin Capsules—USP Monographs. 2002. <http://www.pharmacopoeia.com.cn/v29240/usp29nf24s0_m35930.html>, p. 1-2.
Marques, Margareth. "Dissolution Media Simulating Fasted and Fed States." Dissolution Technologies May 2004, p. 16.
SIF Powder User Guide (http://www.ephares.com/pdf/Phares_SIF_56g_User_Guide.pdf, Version Nov. 8, 2003, Accessed Jun. 16, 2011).
SIF Powder Preparation Protocol (http://www.ephares.com/pdf/Phares_SIF_Powder_Preparation_Protocol.pdf, Accessed Jun. 16, 2011).
FeSSIF/FaSSIF Update (http://www.ephares.com/pdf/FeSSIF_FaSSIF.pdf, p. 1-4, Accessed Jun. 16, 2011).
Dressman et al. (Pharmaceutical Research, vol. 15, No. 5, 1998, 698-705).
Recipes for Physiological Saline (http://www2.ups.edu/faculty/atullis/CAP2007/PHYSIO.%20SALININE.pdf, Accessed Apr. 10, 2012).
Bates et al. (Journal of Pharmaceutical Sciences, vol. 56, Issue 11, Published Nov. 1967, pp. 1492-1495).

*Primary Examiner* — Richard Schnizer
*Assistant Examiner* — Alma Pipic
(74) *Attorney, Agent, or Firm* — Morriss O'Bryant Compagni, PC

(57) ABSTRACT

There are described solid compositions or examining drug solubility comprising bile salts and phospholipids, optionally containing buffer components suitable for preparation of intestinal media that simulate the composition of the intestinal fluids in fasted and fed states.

20 Claims, No Drawings

DISSOLUTION COMPOSITION FOR EXAMINING DRUG SOLUBILITY

CROSS-REFERENCE TO RELATED APPLICATIONS

This application is a continuation of U.S. patent application Ser. No. 12/084,806 filed on May 9, 2008, which is a national stage entry under 35 U.S.C. §371 of International Patent Application No. PCT/EP2006/010809, filed Nov. 10, 2006, published in English as WO 2007/054342 on May 18, 2007, which claims priority to Great Britian Patent Application No. 0522942.2, filed on Nov. 10, 2005, the entirety of each of which is incorporated by this reference.

FIELD OF THE INVENTION

This invention relates to solid compositions and method for preparing biorelevant media thereof. More specifically it describes solid dissolution compositions comprising bile salt and phospholipid complexes which are added to water or aqueous media for preparing simulated intestinal fluids which mimic the fasted and fed states. The media may be used to examine the solubility and dissolution characteristics of poorly water-soluble active compounds and formulations.

BACKGROUND TO THE INVENTION

In vitro dissolution tests using aqueous, acid or alkaline media are carried out in formulation development and for controlling routine inter and intra batch variation of oral dosage forms such as tablets and capsules. Dissolution media which simulate gastrointestinal fluid may include surfactants and solubilisers such as sodium dodecyl sulphate (SDS) and non ionic surfactants. They mimic sink conditions for determining the dissolution profiles of poorly soluble compounds and drug formulations. Dissolution tests using different concentrations of sodium dodecyl sulphate may be employed to evaluate dissolution characteristics, as suggested, e.g., in a monograph on Griseofulvin capsules in "USP 24, page 789". It is however recognised that SDS media are not physiologically relevant and may not forecast in vivo pharmacokinetic profiles reliably. Therefore modified or biorelevant gastrointestinal media comprising physiologically more relevant solubilisers such as lecithin, lysolecithin, bile salts, mono glycerides, fatty acids and mixed micelles thereof have been proposed to better simulate the fasted and fed states.

PRIOR ART

The dissolution media can have a large impact on the pharmacokinetic studies performed to optimise dosing conditions and product formulation. In "Dissolution Technologies, May (2004), page 16" biorelevant media are described to examine the solubility and dissolution characteristics of lipophilic compounds and for studying the effect of food intake on the dissolution rate of lipophilic drugs. The biorelevant intestinal media proposed known as FaSSIF (Fasted State Simulated Intestinal Fluid) and FeSSIF (Fed State Simulated Intestinal Fluid) contain sodium taurocholate and lecithin mixed micelles which have osmolality and pH values that simulate intestinal fluid either in the fasted or fed states. They are prepared freshly, essentially from an emulsion (o/w type) of a water immiscible solvent by removing chlorinated solvent. The main drawback is that the method is not expedient, versatile or cost efficient for routine laboratory use. Coalescence of the dispersed globules in a binary emulsion system as the solvent is removed may result in a heterogeneous population of micelles and mixed micelles. Partitioned solvent between the resultant lipid micelles and mixed micelles and external aqueous phase is not easy to remove entirely. Residual solvent may affect solubility and dissolution profiling of lipophilic compounds which are poorly water soluble. For reproducible data, FaSSIF and FeSSIF media and similar solutions which contain bile salts and phospholipids, as suggested in "Advanced Drug Delivery Reviews 50 (2001), pages 127-147", may not have sufficient shelf-life for storage and off-the-shelf use due to micelle aggregation, lipid oxidation, hydrolysis and microbial contamination. Therefore they have to be freshly prepared.

SUMMARY

The present invention describes novel solid dissolution compositions (SDC) comprising essentially combinations of at least one bile salt and at least one phospholipid and a method for preparing large scale commercial quantities of particulate compositions by removing solvent from solutions or homogeneous dispersions comprising said bile salt and phospholipid. It further describes a robust and reproducible method for preparing modified media or biorelevant dissolution media over wide pH (1 to 10) and osmolality (0 to 800 mOsmol/kg) ranges. Furthermore the SDC may also be used to prepare simulated intestinal fluids (SIF) within the pH (about 5 to about 7.5) and osmolality values of natural intestinal fluid in the fasted (about 270 mOsmol/kg) or fed states (about 670 mOs-mol/kg). Simulated intestinal fluid may be used for assessing the in vitro dissolution characteristics of poorly water soluble active compounds and lipophilic formulations and for correlation of data with in vivo pharmacokinetics profiles under fasted or fed conditions. The information obtained may be useful for QC release purposes in development and commercial batches and to assess bioequivalence of post-approval formulation changes in certain kinds of drugs.

In one aspect the invention concerns a solid dissolution composition (SDC) which may be either compacts or powders comprising essentially at least one bile salt preferably sodium taurocholate and at least one phospholipid, preferably monoacyl phospholipids, preferably mixtures of diacyl and monoacyl phospholipids comprising 10% to 90% w/w of monoacyl phospholipids. The mole ratio of bile salt to phospholipid therein may be broadly between 1:1 to 20:1. Preferably it is between 1:1 to 10:1 for biorelevant media generally. More specifically for preparing intestinal fluids that simulate the fasted and fed states in the upper small intestines the mole ratio of bile salt to phospholipid in the SDC is preferably about 2:1 to 6:1. Preferably the mole ratio is 4:1. However ratios outside this range may be used.

SDC are preferably free flowing or waxy powders which may be complexes, coprecipitates, granulates and lyophilised compositions comprising at least one bile salt and at least one phospholipid. The solid compositions are prepared from hydrophilic or lipophilic organosolvents, monophasic water-solvent solutions, water alone and homogeneous aqueous dispersions after solvent removal and further drying. Optionally buffers and osmotic agents may be included before or after solvent removal or drying. Preferably the SDC is sieved to obtain mean particle diameters within the range 0.5 mm to 5 mm.

In a further aspect solid compositions from large scale batches with defined bile salt:phospholipid ratios between preferably 1:1 to 10:1 are added to either water or aqueous buffer media to prepare biorelevant media and simulated intestinal fluids (SIF). The media may contain from 0.1% w/v to 5% w/v bile salt and phospholipid combinations spanning pH 1 to pH 10 and osmolality 0 mOsmol/kg to 800 mOsmol/kg. Given that the values cover much broader ranges than those found under natural conditions in man and non human species, SDC may be used for preparing all types of dissolution media other than biorelevant or simulated upper small intestinal media.

In another aspect aliquots from SDC with similar bile salt:phospholipid ratios may be packed into suitable air tight bulk containers or unit packs which may be jars or wide mouth re-sealable glass or plastic containers with lids for distribution and long term storage and laboratory use.

Solid Dissolution Composition

Accordingly the invention describes a solid dissolution composition for preparing biorelevant media to evaluate the solubility and dissolution characteristics of poorly water soluble pharmacologically or physiologically active compounds and formulations essentially comprising:
(a) at least one bile salt
(b) at least one phospholipid.

The invention describes a solid dissolution composition for preparing biorelevant media to evaluate the solubility and dissolution characteristics of poorly water soluble pharmacologically or physiologically active compounds and formulations essentially comprising:
(a) at least one bile salt
(b) at least one phospholipid wherein the mole ratio of said bile salt to said phospholipid is 4:1.

The invention further describes a solid dissolution composition for preparing biorelevant media to evaluate the solubility and dissolution characteristics of poorly water soluble pharmacologically or physiologically active compounds and formulations comprising:
(a) at least one bile salt
(b) at least one phospholipid and
(c) buffer components and osmotically active agent.

A solid dissolution composition is described for preparing biorelevant media to evaluate the solubility and dissolution characteristics of poorly water soluble pharmacologically or physiologically active compounds and formulations comprising:
(a) at least one bile salt
(b) at least one phospholipid wherein the mole ratio of said bile salt to said phospholipid is between 1:1 and 10:1
(c) buffer components and osmotically active agents.

In a preferred embodiment said bile salt is sodium taurocholate and said phospholipid is a phospholipid selected from the group consisting of diacyl phospholipids, monoacyl phospholipids, mixtures of diacyl phospholipids and monoacyl phospholipids containing 10% to 90% by weight of monoacyl phospholipids, lecithin, enzyme hydrolysed lecithin.

Another preferred embodiment is a solid dissolution composition for preparing biorelevant dissolution media to evaluate the solubility and dissolution characteristics of poorly water soluble pharmacologically or physiologically active compounds and formulations comprising:
(a) at least one bile salt
(b) at least one monoacyl phospholipid
(c) at least one fatty acid wherein the mole ratio of monoacyl phospholipid to fatty acid is between 1:10 and 10:1.

Another preferred embodiment is a solid dissolution composition for preparing biorelevant dissolution media to evaluate the solubility and dissolution characteristics of poorly water soluble pharmacologically or physiologically active compounds and formulations comprising:
(a) at least one bile salt
(b) at least one monoacyl phospholipid
(c) at least one fatty acid wherein the mole ratio of monoacyl phospholipid to fatty acid is 1:1 and the molar ratio of said bile salt and monoacyl phospholipid is 4:1.

Another preferred embodiment is a solid dissolution composition for preparing biorelevant media to evaluate the solubility and dissolution characteristics of poorly water soluble pharmacologically or physiologically active compounds and formulations comprising:
(a) at least one bile salt and
(b) at least one monoacyl phospholipid
(c) at least one fatty acid selected from the group consisting of lauric, myristic, palmitic, oleic, arachidonic acid wherein the mole ratio of monoacyl phospholipid to fatty acid is between 1:10 and 10:1.

In a preferred embodiment the bile salt to phospholipid mole ratio is between 2:1 and 6:1.

In a further embodiment the solid dissolution composition comprises particles with mean particle diameters between 0.5 mm and 5 mm.

Method for Preparing SDC

An embodiment describes a method for preparing a solid dissolution composition which comprises:
(i) dissolving or dispersing homogeneously essentially at least one bile salt and at least one phospholipid in organosolvent, water-solvent solution or water
(ii) removing the liquid to obtain a solid composition.

An embodiment describes a method for preparing a solid dissolution composition which comprises:
(i) dissolving or dispersing at least one bile salt and at least one phospholipid in the mole ratio 1:10 to 10:1 in organosolvent, water-solvent solution or water
(ii) removing the liquid to obtain a solid composition.

Another embodiment describes a method for preparing a solid dissolution composition which comprises:
(i) dissolving or dispersing essentially at least one bile salt and at least one phospholipid in organosolvent, water-solvent solution or water
(ii) removing the organosolvent, water-solvent solution or water using a method selected from the group of solvent removal methods consisting of evaporation under ambient or elevated temperatures and optionally vacuum; lyophilisation; spray drying; spray granulation.

Another embodiment describes a method for preparing a solid dissolution composition which comprise:
(i) dissolving or dispersing sodium taurocholate and at least one phospholipid selected from the group consisting of lecithin, enzyme hydrolysed lecithin, diacyl phospholipids, monoacyl phospholipids, mixtures of diacyl and monoacyl phospholipids in organosolvent, water-solvent solutions or water wherein the mole ratio of sodium taurocholate to said lipid is between 1:1 and 10:1 further comprising at least one fatty acid wherein the mole ratio of mono acylphospholipid to fatty acid is between 1:10 to 10:1
(ii) removing the liquid to obtain a solid composition An embodiment describes a method for preparing said solid dissolution composition wherein the mean particle size of the powders is between 0.5 mm and 5 mm.

A preferred embodiment describes a method for preparing said solid dissolution composition wherein the powders are sieved and the mean particle size of the powders is between 0.5 mm on 5 mm.

Method for Preparing Gastrointestinal Media

An embodiment describes a method for preparing biorelevant gastrointestinal media which comprises dissolving a solid dissolution composition containing at least one bile salt and at least one phospholipid with mole ratio between 1:10 and 10:1 optionally buffer components and osmotic agents in water or aqueous media at ambient temperatures up to 40° C. optionally employing high speed stirring wherein said gastrointestinal media is a dispersion or solution characterised by:

(a) 0.1% w/v to 5% w/v of said bile salt and said phospholipid
(b) micelles or mixed micelles with mean particle diameters between 0.1 nm and 100 nm
(c) pH between pH 1 to pH 10
(d) osmolality between 0 mOsmol/kg and 800 mOsmol/kg Method for Preparing Fasted & Fed SIF An embodiment describes a method for preparing biorelevant gastrointestinal media at ambient temperatures up to 40° C. simulating fasted state intestinal fluid which comprises dissolving a solid dissolution composition containing at least one bile salt and at least one phospholipid with mole ratio between 2:1 and 6:1 optionally buffer components and osmotic agents in water or aqueous media optionally employing high speed stirring wherein said fasted state SIF media is a dispersion or solution characterised by:

(a) 0.1% w/v to 1% w/v of said combined bile salt and said lipid
(b) micelles or mixed micelles with mean particle diameters between 2 nm and 5 nm
(c) pH adjusted to 6.5±0.5
(d) osmolality 270±20 mOsmol/kg Another embodiment describes a method for preparing biorelevant gastrointestinal media at ambient temperatures up to 40° C. simulating fed state intestinal fluid which comprises dissolving a solid dissolution composition containing at least one bile salt and at least one phospholipid with mole ratio between 2:1 and 6:1 optionally buffer components and osmotic agents in water or aqueous media optionally employing high speed stirring wherein said fed state SIF media is a dispersion or solution characterised by:

(a) 0.2% w/v to 2.5% w/v of said bile salt and said phospholipid
(b) micelles or mixed micelles with mean particle diameters between 2 nm and 5 nm
(c) pH adjusted to 5±0.5
(d) osmolality 670±20 mOsmol/kg

DETAILED DESCRIPTION

In this specification, the following definitions apply:

"Low water solubility" and "poorly water soluble" means any compound that requires more than 10 parts of water to dissolve 1 part of the compound. It spans the definitions between sparingly soluble (from 10 to 30) to very slightly soluble (from 1000 to 10 000) and practically insoluble or insoluble (10 000 and over) as defined in USP 24. The term includes hydrophobic or lipophilic or amphipathic compounds.

"phospholipids" include diacyl and monoacyl phospholipids and glycolipids. Other lipids which can used in combination with phospholipids are fatty acids, mono, di and tri glycerides and cholesterol.

"Active compounds" include compounds that are pharmacologically or physiologically active. The term includes but is not limited to pharmacologically active, poorly water soluble substance which are drug substances of e.g the class of CNS (Central Nervous System), CVS (Cardiovascular System), anti-cancer etc. compounds. Physiologically active, poorly water soluble, substances are nutrition components like e.g., fat soluble vitamins, carotenoids, highly unsaturated fatty acids, CoQ-10, flavonoids etc.

Solid Dissolution Composition

An object of the invention is to utilise SDC which essentially comprise at least one bile salt combined with at least one phospholipid for preparing biorelevant media generally. The phospholipid may be lecithin, enzyme hydrolysed lecithin, diacyl phospholipids, preferably monoacyl phospholipids, more preferably mixtures of diacyl phospholipds and monoacyl phospholipids comprising 10% to 90% by weight monoacyl phospholipids. Bile salts are surprisingly effective for modifying the soft waxy nature of lecithin and phospholipids to a solid state without additional excipients. Monoacyl phospholipids are present in natural duodenal fluids secreted into bile as diacyl phospholipids. Diacyl phospholipids are subjected to enzyme hydrolysis by phospholipases to liberate monoacyl phospholipids and free fatty acids. Therefore monoacyl phospholipids may be preferred to diacyl phospholipids alone to mimic intestinal fluids more closely. SDC may further comprise fatty acids and optionally cholesterol, mono, di and triglycerides in addition to bile salts and mixtures of diacyl phospholipids and monoacyl phospholipids. The mole ratio of fatty acids to monoacyl phospholipids is between 1:10 to 10:1. Preferably between 1:2 and 2:1, more preferably 1:1. SDC may comprise optionally variable amounts of excipients, buffers, osmotic agents. The buffers and osmotic agents may be added before or after preparing the solid compositions.

Generally the SDC may contain less than about 20% by weight water or residual solvent, preferably less than 5%.

It should be understood that the main purpose of the invention is to provide stable solid compositions that may be prepared cost efficiently in bulk quantities and stored, thereby offering maximum flexibility and convenience for preparing reproducible media as and when required. Biorelevant media may be prepared by adding SDC to water or aqueous media making it unnecessary to prepare fresh media using solvent removal every time.

SDC may be used for preparing media wherein the mole ratio of bile salt to phospholipid is broadly between 1:1 to 20:1, preferably 1:1 to 10:1 over the range of pH values between 1.0 and 10 and osmolality values between 0 mOsmol/kg and 800 mOsmol/kg. Preferably SDC consisting of bile salt and lipid with mole ratios between 2:1 and 6:1 (approx wt ratio 2:1 to 4:1, based on the MW of sodium taurocholate), more preferably in the region of 4:1 (approx wt ratio 2.8:1 based on the MW of sodium taurocholate) are used to prepare bio-relevant and simulated intestinal fluid media containing 0.1% to 5% w/v of bile salt and phospholipids.

Method for Preparing SDC

Preferably the SDC is prepared by dissolving or dispersing the bile salt and phospholipid in organosolvent, water-solvent solution, or water, optionally with buffer and osmotic agents. The organosolvent is preferably a suitable hydrophilic volatile solvent, preferably an alkanol, alkanol-water, more preferably a mixture of ethanol and water may be used. Alternatively the powder mixtures may be homogeneously dispersed in water, or water-alkanol solution followed by removal of the solvent and/or water to yield a solid composition. Organosolvents such as methylene chloride, tetrahydrofuran, may be used with small amounts of water to dissolve the bile salt and lipid with the proviso that the water-solvent mixture is monophasic (solution) and an o/w emulsion is not formed during solvent removal.

The SDC may be prepared by removing the liquid using a method selected from solvent removal methods consisting of evaporation under ambient or elevated temperatures optionally under vacuum; granulation and drying with or without vacuum; solvent precipitation using an immiscible solvent, collecting the precipitate and freeing solvents from the precipitate; lyophilisation; spray drying; spray granulation.

Preferably the solid compositions are further sieved or screened to prepare free flowing or waxy powder compositions and may be filled into bulk containers or filled into resealable jars and smaller containers, sachets, or they may be compacted. The mean particle size of the powders is between 0.5 mm to 5 mm, preferably between 1 mm to 2 mm. The powders offer a large surface area for rapid dissolution.

Biorerevant Dissolution Media

SDC spontaneously form compositionally homogeneous micelle dispersions when dissolved or dispersed in water or aqueous buffer-salt solutions at ambient temperatures up to 40° C. High energy input is not required for preparing the micelle dispersions. Optionally Utra Turrax or an impeller type mixer may be employed at moderate to high speeds to facilitate dispersion of larger amounts of SDC to standardise the process under ambient temperatures up to 40° C.

Dissolution media may be prepared by dissolving or dispersing the desired amount of SDC essentially containing bile salts and phospholipids combinations broadly between 1:1 and 20:1 mole ratios in water or aqueous media. The resultant concentration of bile salt and lipids in biorelevant media may be between 0.1% w/v to 10% w/v. Preferably the amount is 0.1% w/v to 5% w/v at pH between 1 and 10 and osmolality between 0 mOs-mol/kg and 800 mOsmol/kg.

Simulated intestinal fluid (SIF) media may be prepared by dissolving or dispersing the desired amount of SDC essentially containing bile salts and lipids combinations with mole ratios between 1:1 and 10:1, preferably between 2:1 and 6:1 mole ratios, more preferably 4:1, in water or aqueous media.

The resulting concentration of bile salt and phospholipid in fasted state SIF may be between 0.1% to 1% w/v at pH 6.5±0.5 and osmolality of about 270±20 mOsmol/kg to simulate natural fasted conditions in upper small intestines.

The resulting concentration of bile salt and phospholipid in fed state SIF may be between 0.2% to 2.5% w/v at pH 5±0.5 and osmolality of about 670±20 mOsmol/kg to simulate natural fed conditions in upper small intestines.

Typically SIF comprises 0.22%±20% w/v bile salt and phospholipid combinations wherein the mole ratio is 4:1 to simulate fasted state conditions at pH 6.5±0.5 and osmolality 270±20 mOsmol/kg.

Typically Fed state SIF comprises 1.12%±20% w/v combined bile salt and phospholipid at pH 5.0±0.5 and osmolality 670±20 mOsmol/kg.

The amount of combined bile salts and phospholipid, pH and osmolality values described are typical values generally employed in biorelevant media which simulate intestinal fluids. Different values outside of these ranges may be used to reflect the wide variations in natural gastrointestinal media between human individuals and animals and in the fasted and fed states.

Optionally buffers, salts and osmoregulating agents may be present in the SDC. Preferably to allow maximum flexibility they are added separately to water or aqueous media for preparing the biorelevant media. Alternatively SDC may be added to standard buffer solutions at pH range 1.2 to 6.8 with same ionic strength as in USP, for example.

Optionally to simulate the fed state, food and digestive components such as fats (e.g., monoglycerides, diglycerides, triglycerides), carbohydrates (poly and oligo saccharides), proteins e.g. from milk), enzymes (such as lipases, proteases) may be included to mimic even more closely natural intestinal fluid.

The unique combination of bile salt and lipid in the SDC which may be a homogeneous complex or pro-micelle composition may enable compositionally homogeneous micelles and mixed micelles dispersions to be prepared with a single population and a narrow particle size distribution. The mean particle diameter of the micelles in the biorelevant media is below 250 nm, preferably below 100 nm, preferably below 50 nm, preferably between 0.5 nm to 50 nm, more preferably between 0.1 nm to 25 nm. Preferably the micelle dispersions are clear to hazy depending on the amount of SDC used and the bile salt to phospholipid ratio therein. The volume of dissolution medium recommended for dissolution studies is 500 mL; 900 mL or 1000 mL (USP). SDC may be used to prepare biorelevant media in place of surfactants such as SDS for in vitro dissolution studies. Biorelevant media can provide a more accurate simulation of pharmacokinetic profiles than simulated gastric fluid or simulated intestinal fluid. Smaller volumes of biorelevant media down to 10 mL may be employed for dissolution studies across the pH range pH 1-10 and osmolality 0 mOsmol/kg to 800 mOsmol/kg.

The biorelevant media in this invention are suitable to characterise the dissolution profiles of poorly water soluble compounds and formulations in terms of in vitro-in vivo correlation and food effects i.e. fasted and fed states. The invention further describes a convenient in-situ method for preparing reproducibly biorelevant media comprising standardised and homogeneous bile salt/phospholipid micelle and mixed micelle suspensions for biorelevant in vitro dissolution tests suitable for cGMP level Quality Control.

The SDC and biorelevant media thereof are particularly suitable to evaluate in vitro solubility and dissolution rates of poorly water soluble and pharmacologically or physiologically compounds. They are particularly suitable for in vitro pharmacokinetic profiling and in vivo correlation of Class 2 and Class 4 compounds according to current BCS classification (Amidon G L et al, Pharm. Res. (2004) vol 12, nr 3, pp 413-420). Furthermore biorelevant media prepared with SDC may be used to evaluate the dissolution kinetics of water soluble compounds formulated as sustained or long acting compositions comprising lipophilic excipients such as polymers and high melting point fats and waxes. Dissolution rates of the pure compounds and formulations e.g. tablets, capsules, powders, dragees may be evaluated using pharmacopoeial methods.

It is to be understood that SIF prepared from SDC may also be used as a dilution medium and carrier for poorly soluble active compounds and formulations thereof for oral use. Pharmacologically active poorly soluble compounds include but are not limited to CNS, CVS, anti-cancer compounds. Other physiologically that come to mind are active, poorly soluble compounds which include nutrition components like fat soluble vitamins, carotenoids, highly unsaturated fatty acids, CoQ-10, flavonoids.

A list of preferred components for preparing solid dissolution compositions is set out below.

Bile Salt

Sodium cholate, sodium taurocholate, sodium glycocholate, sodium deoxycholate, sodium taurodeoxycholate, sodium glycodeoxycholate, sodium ursodeoxycholate, sodium chenodeoxycholate, sodium taurochenodeoxycholate, sodium glyco chenodeoxycholate, sodium cholylsarcosinate, sodium N-methyl taurocholate. The cholates may be from natural, synthetic or semi-synthetic sources. If the cholate is natural, it should be preferably from porcine or TSE/BSE-free bovine sources.

Phospholipids

Phospholipids include natural lecithins from egg, milk, soy, sunflower, oat, etc. Lecithins contain mixtures of phospholipids. The phospholipds include phosphatidylcholine (PC), phosphatidylethanolamine (PE), phosphatidylserine (PS), phosphatidylinositol (PI), phosphatidylglycerol (PG), and their monoacyl derivatives. Cardiolipin, sphingomyelin, and their monoacyl derivatives are phospholipids, whilst glycolipids may be regarded as a 'phospholipid'. The phospholipids may be purified or fractionated lecithins which contain from 10 wt % to 100 wt % of PC, well defined in terms of purity. Enzyme hydrolysed soya lecithins, monoacyl phospholipids on their own, or preferably mixtures of monoacyl phospholipids and diacyl phospholipids are preferred which contain defined amounts of diacyl phospholipids and their monoacyl derivatives wherein the amount of monoacyl phospholipids lipids chiefly monoacyl phosphatidylcholine is between 10 wt % to 90 wt %. Enzyme hydrolysis is carried out on diacyl phospholipids with phospholipase A2 and the compositions are purified or fractionated to obtain the desired amount of monoacyl phospholipids in the mixture.

Examples of other lipids which may be used preferably in combination with the mixture of the bile salt with diacyl and/or monoacyl phospholipids are, fatty acids and non polar lipids such as cholesterol.

Buffer and Osmoregulators

Buffers include but are not limited to phosphate salts, TRIS salts, citric acid or citrate salts, bicarbonates, HEPES, histidine, 1 N HCl or 1 N NaOH solutions may be used to adjust the final pH values between pH 1 and pH 10. Furthermore the SDC and aliquots thereof may be added to custom made or standard dissolution media preferably within the pH range 1.2 to 6.8 and the same ionic strength as e.g. USP. Aqueous media comprise pre-mixed or pre packed solutions which include but are not limited to 0.05 M potassium phosphate pH 6.8; 0.05 N potassium phosphate pH 7.2; 0.05 N potassium phosphate pH 7.4; 0.05 M acetate Buffer pH 5. Sodium bicarbonate may also be used as buffer component. Osmoregulators include KCl and sugars.

The following examples illustrate the invention without limiting the scope thereof.

EXAMPLE 1

A solid dissolution composition (SDC) is prepared by dissolving 2.95 g of sodium taurocholate and 1.056 g Egg PC (Lipoid) in 30 ml ethanol at 50° C. The solvent is removed using a rotavap at 50° C. and 150 mbar and drying under high vacuum overnight to prepare a solid dissolution composition.

A fasted state SIF medium comprising 1.12 g of the resulting free flowing bile salt/lecithin powder composition dissolves immediately in a medium containing 3.093 g NaCl (Fluka), 0.174 g NaOH (RdH) and 1.977 g $Na_2PO_4.H_2O$ (RdH) per 0.5 liter water and the pH is adjusted to pH 6.5 with NaOH or HCl (1 N).

Measurement of the particle size using a Malvern Particle Sizer (Mastersizer) shows the presence of a homogenous population of micelles of around 2 nm mean particle diameter.

EXAMPLE 2

A solid dissolution composition (SDC) is prepared by dissolving 16.5 g of sodium taurocholate and 5.9 g Egg PC (Lipoid) in 150 ml ethanol at 50° C. The solvent is removed using a rotavap at 50° C. and 150 mbar and drying under high vacuum overnight.

For preparation of fed state SIF medium 11.2 g of the resulting free flowing bile salt/lecithin powder composition dissolves immediately in 1 L medium containing 11.874 g NaCl (Fluka), 4.04 g NaOH (RdH) per liter water. 8.65 g glacial acetic are added and the pH is adjusted with NaOH or HCl (1 N) to achieve a pH value of 5.00.

Measurement of the particle size using a Malvern Particle Sizer (Mastersizer) shows the presence of a homogenous population of micelles of around 2 nm mean particle diameter.

EXAMPLE 3

As in Ex 2 the solid composition is prepared by dissolving the sodium taurocholate and Egg PC in 10% ethanol or water and the solvent is removed by freeze or spray drying.

EXAMPLE 4

As in Ex 2 the solid composition is prepared by dissolving the sodium taurocholate and soya PC comprising 95% phosphatidyl choline in 10% ethanol or water and the solvent is removed by freeze or spray drying.

EXAMPLE 5

As in Ex 2 the solid composition is prepared by dissolving the sodium taurocholate and a mixture of diacyl and monoacyl phospholipids containing 80% of monoacyl phospholipids and 20% of diacyl phospholipids in 10% ethanol in water or water and the solvent is removed by freeze or spray drying.

EXAMPLE 6

For comparison with Example 1, a FASSIF medium is prepared by dissolving 3.3 g of sodium taurocholate in 500 mL blank FaSSIF (prepared by dissolving 1.74 g NaOH, 19.77 g $NaH_2PO4.H_2O$ and 30.93 g of NaCl in 5 L purified water; pH is adjusted to pH 65. using 1 N NaOH or HCl) and 11.8 mL of a solution containing 100 mg/mL egg lecithin (Lipoid) in methylenechloride (RdH), forming an emulsion. The methylenechloride is eliminated form the emulsion under vacuum at about 40° C. at 250 mbar for 15 minutes. The volume was adjusted to 2 L with blank FaSSIF.

Measurement of the particle size using a Malvern Particle Sizer (Mastersizer) shows the presence of heterogeneous population of micelles comprising three populations with 0.5 nm, 7.5 nm, and 250 nm mean particle diameter.

The invention describes substantially homogeneous solid compositions comprising bile salts and phospholipids optionally containing buffer components suitable for preparation of biorelevant gastrointestinal media that simulate the composition of the intestinal fluids in fasted and fed states.

What is claimed is:

1. A method of determining solubility or dissolution of a pharmacological compound, comprising:
    preparing an aqueous medium containing at least one buffer component and at least one osmotic agent;
    adding a homogeneous solid dissolution composition in a granular or powder form comprising at least one bile salt and at least one phospholipid to the aqueous medium to form a simulated gastrointestinal medium;
    adding at least one of a pharmacological compound, a physiological compound and a dosage form to the simulated gastrointestinal medium to determine a solubility or dissolution characteristic of the pharmacological compound, physiological compound or dosage form.

2. The method of claim 1, wherein adding the dissolution composition comprises adding the homogeneous solid dissolution composition to the aqueous medium wherein the at least one bile salt and at least one phospholipid have a mole ratio between about 1:1 and 20:1.

3. The method of claim 1, further comprising forming the simulated gastrointestinal medium with 0.1% w/v to 5% w/v of the at least one bile salt and the at least one phospholipid, micelles or mixed micelles with mean particle diameters below 100 nm, a pH between about pH 1 and pH 10 and an osmolality less than about 800 mOsmol/kg.

4. The method of claim 1, further comprising simulating a fasted state intestinal fluid by adjusting the pH to between about 6.0 and 7.0 and producing the simulated gastrointestinal medium with a combined weight per volume of about 0.1% to 1% of the at least one bile salt and the at least one phospholipid.

5. The method of claim 4, further comprising producing the simulated gastrointestinal medium with an osmolality of between about 250 and 290 mOsmol/kg.

6. The method of claim 1, further comprising simulating a fed state intestinal fluid by adjusting the pH to about 4.5 to 5.5 and producing the simulated gastrointestinal medium with a combined weight per volume of about 0.2% to 2.5% of the at least one bile salt and the at least one phospholipid.

7. The method of claim 6, further comprising producing the simulated gastrointestinal medium with an osmolality of about 650 to 690 mOsmol/kg.

8. The method of claim 1, further comprising providing the solid dissolution composition with a water content of less than about 5% by weight.

9. The method of claim 1, further comprising selecting the at least one phospholipid from the group of phospholipids consisting of lecithin, enzyme hydrolyzed lecithin, diacyl phospholipids, monoacyl phospholipids, and a mixture of diacyl phospholipids and monoacyl phospholipids comprising about 10% to 90% by weight monoacyl phospholipids.

10. The method of claim 1, further comprising adding the at least one bile salt and the at least one phospholipid to a liquid selected from the group consisting of organosolvents, water-solvent solutions and water and removing a substantial portion of the liquid for providing the solid dissolution composition.

11. The method of claim 1, further comprising adding the at least one bile salt, the at least one phospholipid and at least one added component selected from the group consisting of fatty acids, cholesterols, a monoglyceride, a diglyceride and a triglyceride in a liquid selected from the group consisting of organosolvents, water-solvent solutions and water and removing a substantial portion of the liquid for providing the solid dissolution composition.

12. The method of claim 1, further comprising providing the solid dissolution composition in the form of a free flowing powder.

13. The method of claim 1, further comprising providing the bile salt and the at least one phospholipid in a mole ratio of between about 1:1 and 10:1.

14. The method of claim 1, further comprising providing the bile salt and the phospholipid in a mole ratio of about 4:1.

15. The method of claim 1, wherein the bile salt is selected from the group consisting of sodium cholate, sodium taurocholate, sodium glycocholate, sodium deoxycholate, sodium taurodeoxycholate, sodium glycodeoxycholate, sodium ursodeoxycholate, sodium chenodeoxycholate, sodium taurochenodeoxycholate, sodium glyco chenodeoxycholate, sodium cholylsarcosinate, and sodium N-methyl taurocholate.

16. The method of claim 1, further comprising adding at least one fatty acid, wherein the mole ratio of the at least one phospholipid in the form of monoacyl phospholipid to the at least one fatty acid is between about 10:1 and 1:10.

17. The method of claim 16, further comprising providing the monoacyl phospholipid and the at least one fatty acid in a mole ratio of about 1:1.

18. The method of claim 16, further comprising selecting the at least one fatty acid from the group consisting of lauric acid, myristic acid, palmitic acid, oleic acid and arachidonic acid.

19. The method of claim 1, further comprising providing the simulated gastrointestinal medium with at least one additional component selected from a fatty acid, a cholesterol, a monoglyceride, a diglyceride, a triglyceride, a carbohydrate, a protein and an enzyme.

20. The method of claim 1, further comprising providing the solid dissolution composition with at least one component selected from the group consisting of a fatty acid, a cholesterol, a monoglyceride, a diglyceride and a triglyceride.

* * * * *